(12) United States Patent
Baduvamanda et al.

(10) Patent No.: US 7,632,545 B2
(45) Date of Patent: Dec. 15, 2009

US007632545B2

(54) RADIATION SHIELDING COMPOSITION AND A PREPARATION METHOD THEREOF

(75) Inventors: Cariappa Achappa Baduvamanda, Bangalore (IN); Bhaskar Raj, Bangalore (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/125,705

(22) Filed: May 10, 2005

(65) Prior Publication Data

US 2006/0255321 A1    Nov. 16, 2006

(51) Int. Cl.
*B05D 1/02* (2006.01)
*C08L 63/00* (2006.01)
*C08K 3/10* (2006.01)
*B32B 27/20* (2006.01)
*B32B 27/38* (2006.01)

(52) U.S. Cl. .................. 427/427.4; 427/421.1; 523/440; 523/442; 523/457; 523/459

(58) Field of Classification Search ....................... None
See application file for complete search history.

(56) References Cited

U.S. PATENT DOCUMENTS

| 3,438,903 A | * | 4/1969 | Prahl | 252/478 |
| 3,858,050 A | * | 12/1974 | Carlson | 250/515.1 |
| 3,961,123 A | * | 6/1976 | Ohtomo | 442/187 |
| 5,278,219 A | * | 1/1994 | Lilley et al. | 524/439 |
| 2004/0029998 A1 | * | 2/2004 | Tomita et al. | 523/136 |

FOREIGN PATENT DOCUMENTS

| EP | 0628968 A1 | | 12/1994 |
| FR | 2406870 A1 | | 5/1979 |
| FR | 2570001 A1 | | 3/1986 |
| GB | 1137554 A | | 12/1968 |
| JP | 06-051095 | * | 2/1994 |
| JP | 06-180389 | * | 6/1994 |
| JP | 06-249998 | * | 9/1994 |

OTHER PUBLICATIONS

Machine translation of JP 06-051095, provided by the JPO website.*
Machine translation of JP 06-180389, provided by the JPO website.*
Machine translation of JP 06-249998, provided by the JPO website.*
Sieve Conversion Chart, provided by www.qclabequipment.com (no date).*

* cited by examiner

*Primary Examiner*—Michael J Feely
(74) *Attorney, Agent, or Firm*—Peter Vogel, Esq.; William Baxter, Esq.; Michael G. Smith, Esq

(57) ABSTRACT

In one embodiment, a radiation shielding composition comprises lead oxide or lead composite material of predetermined particle size, and an adhesive, wherein the composition comprises free flow property.

9 Claims, 2 Drawing Sheets

RADIATION SHIELDING COMPOSITION AND A PREPARATION METHOD THEREOF

FIELD OF THE INVENTION

This invention relates generally to compositions and methods for shielding radiation, and more particularly, to a radiation shielding composition for an X-ray system and a method for preparing the same.

BACKGROUND OF THE INVENTION

An X-ray generator e.g., a Tube Head (having an X-ray tube and a generator within a housing) is used widely as a compact source for producing high quality X-rays especially, in medical imaging.

During X-ray generation, the X-ray tube generates X-rays in all directions around a focal spot or an X-ray aperture requiring X-ray exposure. However, exposure to even low levels of X-ray radiation may cause undesirable health effects to a user or operator in an X-ray environment.

New generation X-ray systems are often configured to generate X-rays with no drift in dosage quantities to comply with the clinical requirements especially, in bone densitometry. Moreover, regulatory requirements demand for a radiation leakage specification of about 0 to 2 milli Roentgens per hour at the X-ray source surface or at a specified distance from the source.

Thus, sufficient shielding and thereby prevention of exposure to X-ray radiation e.g., in locations other than the focal spot or the X-ray aperture becomes necessary to safeguard the user/operator from undesirable health hazards.

During design, development and manufacture of X-ray generators, the radiation leakage, as measured using standard calibrated dosimeters, typically varies from few milli Roentgens to few tens of milli Roentgens at the generator equipment surface. Generally, correction and thereby control of radiation leakage from the generator equipment surface is frequently carried out to comply with the regulatory requirements and hence provide a controlled and safe X-ray environment.

Conventionally, during design and development of an X-ray generator, correction of radiation leakage from the generator equipment surface is carried out by providing additional shielding in the form of tapes and sheets constructed from molded lead, brass, composites of lead, etc. Although use of lead content sheets enables substantially correcting the radiation leakage, this process involves (i) stripping of the equipment, rework, and addition of lead content sheets, reassembly and retesting of the equipment; (ii) a risk of hazardous handling of lead content sheets; (iii) low aesthetics for packaging; (iv) an increase in weight, contamination of insulating oil and loss of productivity; and (v) space limitations in compact X-ray generators.

Thus, there exists a need for an X-ray shielding composition and a method wherein, the composition and method would provide (i) a quick correction of radiation leakage from the generator equipment surface, especially during design and development; (ii) substantially no risk in handling; (iii) improved aesthetics for the generator package; (iv) no substantial increase in weight; and (v) no space constraints.

BRIEF DESCRIPTION OF THE INVENTION

In one embodiment, a radiation shielding composition comprises lead oxide or lead composite material of predetermined particle size, and an adhesive in free flow form.

In another embodiment, a method of preparing radiation shielding composition includes mixing lead oxide or lead composite material of predetermined particle size with an adhesive in predetermined proportion and stirring the mixture until substantial homogeneity, wherein the resultant mixture is capable of flowing freely.

In yet another embodiment, an X-ray system includes an X-ray source, an enclosure for said X-ray source and a radiation shielding composition coated on the enclosure, wherein the radiation shielding composition is capable of flowing freely.

Compositions, methods and systems of varying scope are described herein. In addition to the aspects and advantages described in this summary, further aspects and disadvantages will become apparent by reference to the drawings and by reading the detailed description that follows.

DETAILED DESCRIPTION OF THE INVENTION

Figure 1:
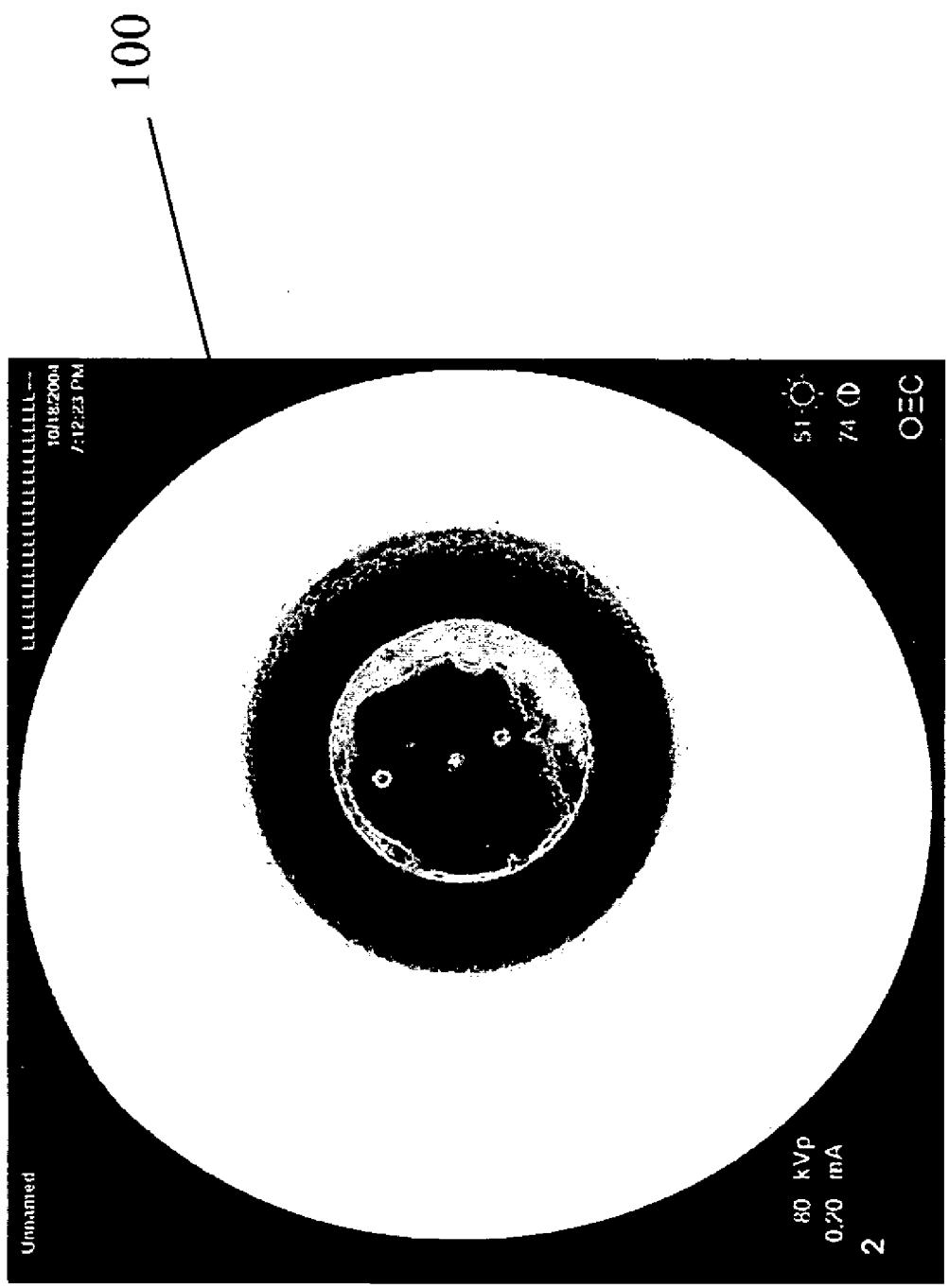
FIG. 1 shows an example of an X-ray image without shielding.

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Various embodiments of this invention provide a radiation shielding composition for an X-ray generator used in medical imaging. One example of an X-ray generator includes a Tube Head comprising an X-ray tube and a generator within a housing. Examples of use in medical imaging include bone densitometry, CT scanning, mobile radiography, surgical C-Arm, portable X-ray systems, etc.

However, the embodiments are not so limited, and may be implemented in connection with other systems such as, for example, security scanners, industrial inspection systems, gamma ray detectors and various other nuclear and X-ray devices.

In various embodiments, a radiation shielding composition is provided, wherein the composition includes lead oxide and an adhesive, wherein the resulting mixture is capable of flowing freely. In particular, the composition includes lead oxide of predetermined particle size and an adhesive configured in free flow form for shielding radiation.

However, in other embodiments, a radiation shielding composition may include a lead composite material instead of lead oxide or in addition to lead oxide. For example, the lead composite may include at least one element selected from the group consisting of brass, barium, cadmium, titanium and tungsten.

In one embodiment, the particle size of lead oxide is in the range of about 300 to 900 mesh. The lead oxide and the adhesive are in the ratio of about 2:1.

In another embodiment, the particle size of lead composite material is in the range of about 30 to 100 mesh. The lead composite material and the adhesive are in the ratio of about 2:1. In one example, the adhesive may include an epoxy resin. In another example, the adhesive may include epoxy and resin in substantially equal proportion.

It should be noted that the radiation shielding composition according to this invention offers a lightweight solution and can be applied to X-ray equipments using a conventional brush or a simple tool such as an applicator, or from a pressurizing source such as, a spray can. This improves operability without need for special skills for an operator.

It should also be noted that the radiation shielding composition according to this invention can be used with X-ray equipments where it is not possible to insert lead sheets due to space constraints and electrical and mechanical clearance limitations.

In another embodiment, a method for preparing a radiation shielding composition includes mixing lead oxide or lead composite material of predetermined particle size with an adhesive in predetermined proportion and stirring the mixture until substantial homogeneity, wherein the resultant mixture is capable of flowing freely.

In an embodiment, the particle size of lead oxide is in the range of about 300 to 900 mesh. The lead oxide and the adhesive are mixed in the ratio of about 2:1.

In another embodiment, the particle size of lead composite material is in the range of about 30 to 100 mesh. The lead composite material and the adhesive are mixed in the ratio of about 2:1.

In one example, the adhesive includes an epoxy resin.

In another example, the adhesive includes epoxy and resin mixed in substantially equal proportion until exothermic reaction starts taking place and the temperature of the mixture substantially increases.

It should be noted that the resin and epoxy are mixed in substantially equal proportions to achieve homogeneity and substantial hardness after drying.

It should also be noted that the use of lead in particulate form together with adhesive, wherein the resultant mixture is in a free flow form according to this invention enables eliminating the use of lead sheets for shielding X-rays.

The free flow radiation shielding composition according to this invention improves productivity by reducing the rework time significantly.

Yet in another embodiment, an X-ray system includes an X-ray source and an enclosure for the X-ray source. The enclosure includes a coating of radiation shielding composition, wherein the radiation shielding composition comprises free flow property.

For example, the coating may include a thickness of about 0.2 mm.

FIG. 1 shows an example of an X-ray image 100 without shielding.

Figure 2:
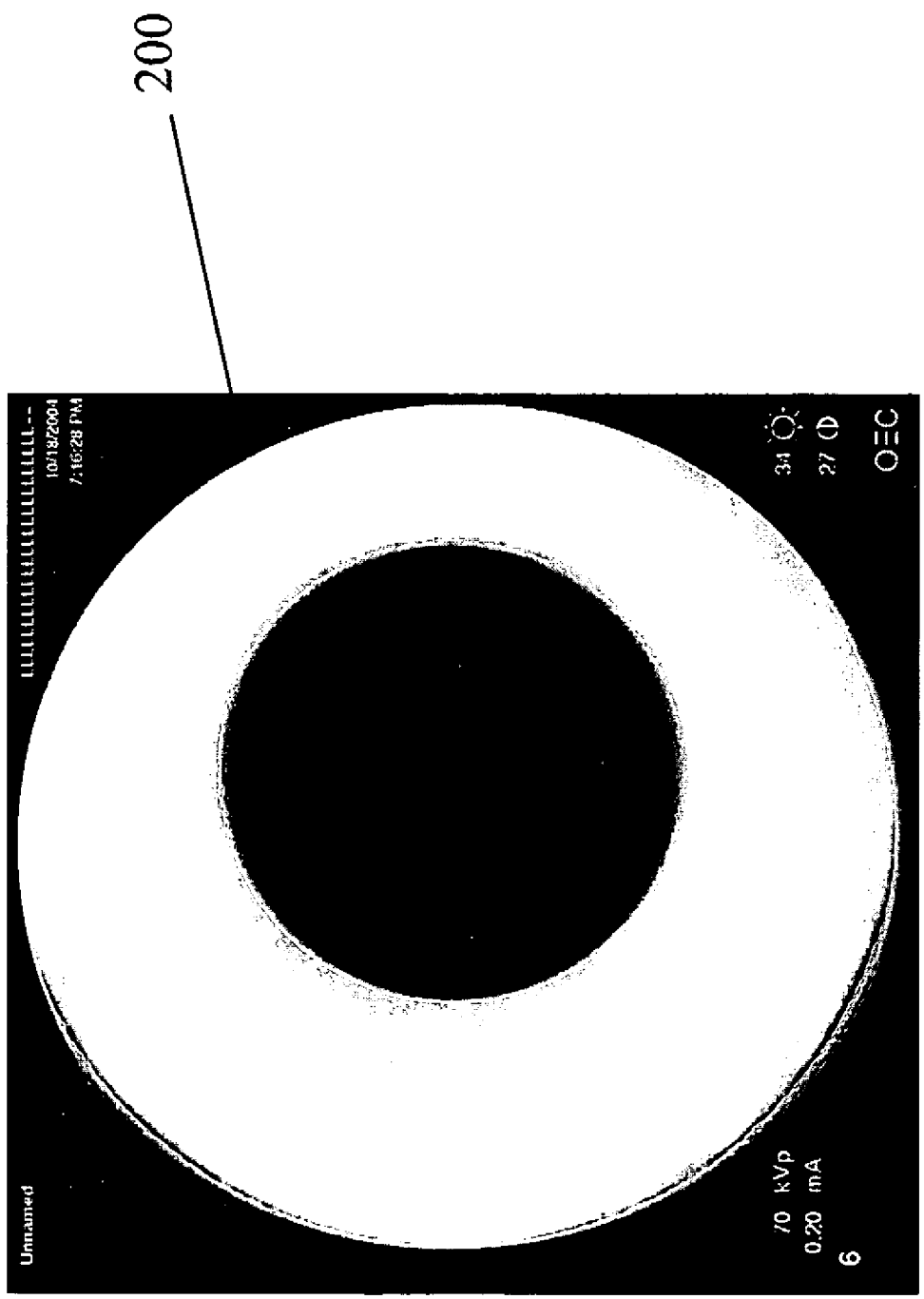
FIG. 2 shows an example of an X-ray image being shielded by the radiation shielding composition according to one embodiment of the present invention.

FIG. 2 shows an example of an X-ray image 200 shielded by a coating of 2.5 mm thickness of free flow radiation shielding composition according to this invention.

It should be noted that a coating of about 2.5 mm of radiation shielding composition according to this invention can shield an X-ray dosage of up to 5000 mR.

For example, a thickness of about 12 microns can shield an X-ray dosage of about 1 to 10 mR.

In another embodiment, the coating of radiation shielding composition may include a coating of at least one of lacquer, varnish and epoxy paint on the radiation shielding composition.

In an embodiment, the radiation shielding composition includes lead oxide and an adhesive.

In an embodiment, the radiation shielding composition includes a lead composite material and an adhesive.

It should be noted that the X-ray generator using the free flow radiation shielding composition according to this invention remains free from lead sheets that are bulky and also reduce thermal property of the generator.

For example, the damages caused in enclosures such as X-ray rooms in clinics and hospitals, metal enclosures for X-ray testing. Lead aprons can be coated with the radiation shielding composition according to this invention, for shielding the leakage or absorbing X-rays.

Thus, various embodiments of this invention describe a radiation shielding composition and a method of preparation thereof. Further embodiments of this invention describe an X-ray system.

While the invention has been described with various specific embodiments, it will be obvious for a person skilled in the art to practice the invention with modifications. However, all such modifications are deemed to be within the scope of the claims.

What is claimed is:

1. A radiation shielding composition consisting of:
   at least one of a lead oxide material of a predetermined particle size and a lead composite material of a predetermined particle size; and an adhesive consisting of an epoxy resin and a second resin, wherein the second resin is co-reactive with the epoxy resin,
   wherein the radiation shielding composition comprises a free flowing property prior to hardening;
   wherein the radiation shielding composition, prior to hardening, is capable of being applied to a substrate from a spray can pressuring source; and
   wherein the radiation shielding composition, when hardened and provided in a coating thickness of about 2.5 mm, is capable of shielding an X-ray dosage of up to 5000 milliRoentgens.

2. The radiation shielding composition according to claim 1 wherein the lead oxide material is present.

3. The radiation shielding composition according to claim 1 wherein both the lead oxide material and the lead composite material are present.

4. The radiation shielding composition according to claim 1 wherein the lead composite material further comprises cadmium.

5. The radiation shielding composition according to claim 1 wherein the lead composite material is present.

6. The radiation shielding composition according to claim 1 wherein the lead composite material further comprises brass.

7. The radiation shielding composition according to claim 1 wherein the lead composite material further comprises titanium.

8. A method for preparing the radiation shielding composition according to claim 1, the method comprising:
   mixing the at least one of a lead oxide material of a predetermined particle size and a lead composite material of predetermined particle size with the adhesive, yielding a mixture; and
   stirring the mixture until the mixture is capable of flowing freely.

9. A method of coating a substrate with the radiation shielding composition according to claim 1, the method comprising:
   spraying the free flowing radiation shielding composition from a spray can pressuring source onto a substrate, yielding a coating thickness of about 2.5 mm; and
   drying the coating, yielding a hardened material capable of shielding an X-ray dosage of up to 5000 milliRoentgens.

* * * * *